United States Patent
Noor et al.

(10) Patent No.: US 11,958,866 B1
(45) Date of Patent: Apr. 16, 2024

(54) SYNTHESIS OF THIAZOLE DERIVATIVES

(71) Applicant: KING FAISAL UNIVERSITY, Al-Ahsa (SA)

(72) Inventors: Awal Noor, Al-Ahsa (SA); Ezzat Khan, Al-Ahsa (SA); Umar Ali Khan, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/381,016

(22) Filed: Oct. 17, 2023

Related U.S. Application Data

(62) Division of application No. 18/131,955, filed on Apr. 7, 2023, now Pat. No. 11,814,399.

(51) Int. Cl.
*C07D 513/04* (2006.01)
*C07D 277/82* (2006.01)

(52) U.S. Cl.
CPC ......... *C07D 513/04* (2013.01); *C07D 277/82* (2013.01)

(58) Field of Classification Search
CPC .......................... C07D 513/04; C07D 277/82
USPC ........................................................ 546/114
See application file for complete search history.

(56) References Cited

PUBLICATIONS

Shroeder, Z.W. et al., "Copper(II)- and Gold(III)-Mediated Cyclization of a Thiourea to a Substituted 2-Aminobenzothiazole" Acta Cryst. C73, pp. 905-910 (2107).
Canudo-Barreras, G. et al., "Gold-Catalyzed 1,3-Thiazine Formation and Uncommon Tautomer Isolation" J. of Organic Chemistry 87: pp. 10747-10754 (2022).

*Primary Examiner* — Kahsay Habte
(74) *Attorney, Agent, or Firm* — Nath, Goldberg & Meyer; Richard C. Litman

(57) ABSTRACT

A synthetic protocol to use a thiourea or urea compound and auric chloride as starting materials to obtain thiazole and benzothiazole derivatives. The synthesis can be conducted at room temperature and the final compound can result from cyclization of the thiourea or urea compound in the presence of an Au salt from the auric chloride.

10 Claims, No Drawings

SYNTHESIS OF THIAZOLE DERIVATIVES

CROSS-REFERENCE TO RELATED APPLICATION

This application is a divisional of U.S. patent application Ser. No. 18/131,955, filed on Apr. 7, 2023, the entire contents of which are incorporated herein by reference.

BACKGROUND

1. Field

The disclosure of the present patent application relates to a novel synthetic method, and particularly to a new synthetic method for making various thiazole derivatives.

2. Description of the Related Art

Thiazoles are 5-membered bioactive organic molecules, with S and N heteroatoms in the ring, and have been found as dynamic tools in medicinal chemistry. Being an integral part of available therapeutics, these compounds are well documented and have been a subject of several patent documents for many years. Their role as anticancer, antiviral, antibacterial, antifungal, and anti-inflammatory agents is well established in the commercial market and the literature. For example, thiazoles appear in bacitracin and penicillin antibiotics and various synthetic drugs. The thiazole family includes antimicrobial agents such as acinitrazole and sulfathiazole, antibiotic penicillin, antidepressant pramipexole, antineoplastic agents such as Bleomycin and Tiazofurin, anti-HIV drug Ritonavir, antiasthmatic drug cinalukast, and antiulcer agent Nizatidine. Thiazole derivatives are also used as non-steroidal immunomodulatory drugs (for instance, Fanetizole) and anti-inflammatory drugs (such as Meloxicam).

Thiazole derivatives have also exhibited anti-fungal, anti-tumor and antiviral activities. Besides the biological activity of the molecules, such thiazole compounds have been used as starting precursors for numerous organic and inorganic reactions. Some of the derivatives have also been applied in the food industry as a flavoring agent.

The thiazole molecule has several reaction sites which make synthesis and its further derivatization a serious challenge. The synthetic challenges followed by target specific biological application of novel thiazole derivatives in pharmaceutical markets has been secured in several patents.

Accordingly, there is a significant need in the art for a new way to reliably obtain such thiazole derivatives using common, low-cost starting materials. Thus, a synthetic process solving the aforementioned problems is desired.

SUMMARY

The present subject matter relates to a synthetic protocol to use cheap starting materials accessible under normal laboratory conditions and to converting them into thiazole and benzothiazole derivatives. The use of the specific starting materials leads to the formation of cationic derivatives which will overcome the problem of least solubility of the derivative in polar solvents and in physiological fluids.

In an embodiment, the present subject matter relates to a process for synthesizing a thiazole, thiadiazole, or benzothiazole derivative, the process comprising: preparing a first solution of a thiourea or urea compound in acetonitrile; preparing a second solution of auric chloride ($HAuCl_4$) in acetonitrile; adding the first solution to the second solution to obtain a reaction mixture; stirring the reaction mixture for at least six hours; filtering the reaction mixture to obtain a solid product; dissolving the solid product in chloroform to obtain a third solution; and recrystallizing the thiazole, thiadiazole, or benzothiazole derivative from the third solution.

In another embodiment, the present subject matter relates to a process for synthesizing N-(2H-thiazolo[3,2-b][1,2,4]thiadiazol-2-ylidene)benzamide comprising reacting 1-Benzoyl-3-(thiazole-2-yl)thiourea with auric chloride according to the following reaction:

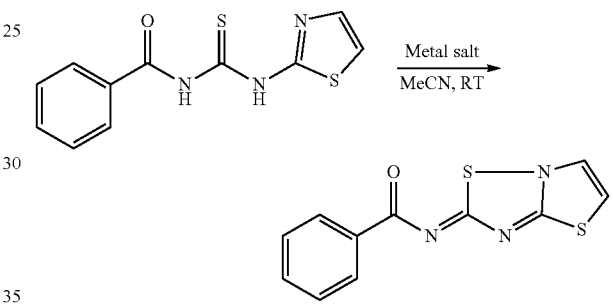

In a further embodiment, the present subject matter relates to a process for synthesizing N-(6-methylthiazolo[4,5-b][1,2,4]pyridin-2-yl)benzamide comprising reacting 1-(6-Methylpyridine-2-yl)-3-benzoylthiourea with auric chloride according to the following reaction:

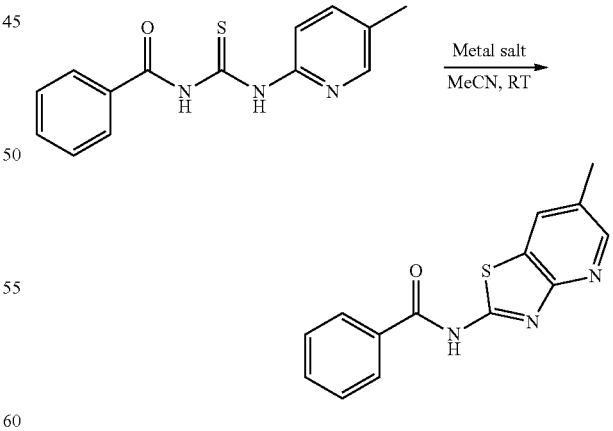

In still another embodiment, the present subject matter relates to a process for synthesizing N-(6-methoxy-3-(4-methoxyphenyl)-3$\lambda^4$-benzo[d]thiazol-2-yl)benzamide gold (III) chloride comprising reacting 1-(Bis(4-methoxyphenyl)-3-benzoylthiourea with auric chloride according to the following reaction:

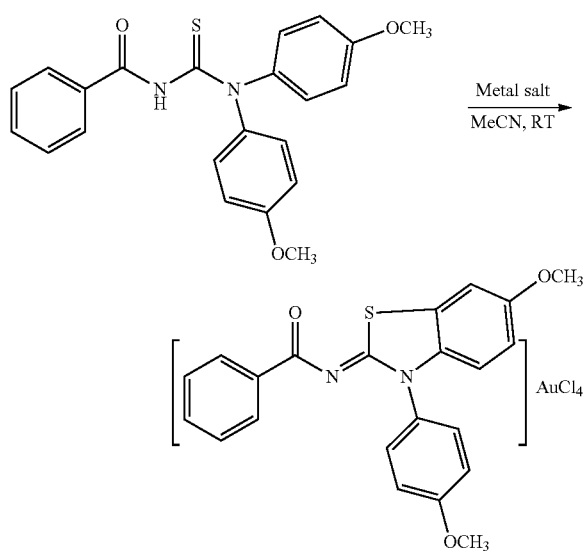

In still yet another embodiment, the present subject matter relates to a process for synthesizing 5-Methyl-N-phenyl-4λ$^4$-[1,2,4]thiadiazolo[2,3-a]pyridine-2-aminegold(III) chloride comprising reacting 1-phenyl-3-(thiazole-2-yl)thiourea with auric chloride according to the following reaction:

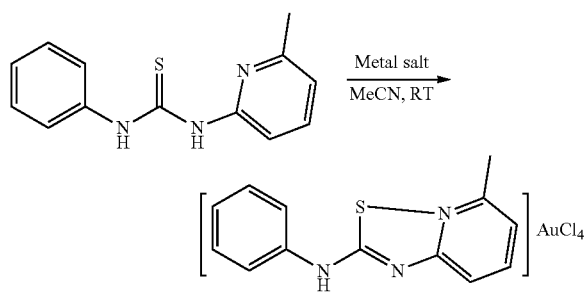

These and other features of the present subject matter will become readily apparent upon further review of the following specification and drawings.

DETAILED DESCRIPTION OF THE PREFERRED EMBODIMENTS

The following definitions are provided for the purpose of understanding the present subject matter and for construing the appended patent claims.

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically infeasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a synthetic protocol to use cheap starting material accessible under normal laboratory conditions and to convert them into thiazole and benzothiazole derivatives. The use of the specific starting materials leads to the formation of cationic derivatives which will overcome the problem of least solubility of the derivative in polar solvents and in physiological fluids.

Various aspects now will be described more fully hereinafter. Such aspects may, however, be embodied in many different forms and should not be construed as limited to the embodiments set forth herein. Rather, these embodiments are provided so that this disclosure will be thorough and complete, and will fully convey its scope to those skilled in the art.

In an embodiment, the present subject matter relates to a process for synthesizing a thiazole, thiadiazole, or benzothiazole derivative, the process comprising: preparing a first solution of a thiourea or urea compound in acetonitrile; preparing a second solution of auric chloride (HAuCl$_4$) in acetonitrile; adding the first solution to the second solution to obtain a reaction mixture; stirring the reaction mixture for at least six hours; filtering the reaction mixture to obtain a solid product; dissolving the solid product in chloroform to obtain a third solution; and recrystallizing the thiazole, thiadiazole, or benzothiazole derivative from the third solution.

In certain embodiments, the thiazole, thiadiazole, or benzothiazole derivative is formed as a result of cyclization of the thiourea or urea compound in the presence of an Au salt from the auric chloride. In this regard, a cyclic group of the thiazole, dithiazole, or benzothiazole derivative is prepared by forming any of a S—N, S—C, S—S, or S—O bond. This is a significant advantage over previously known process, in which only the S—C bond could be used to form the cyclic group.

In further embodiments, C=S groups in the thiourea compound can be selectively converted into forming the thiazole, thiadiazole, or benzothiazole derivative. In other embodiments, all steps of the reaction and process can be carried out at room temperature. In certain embodiments, the present synthesis methods can provide a yield of the thiazole, thiadiazole, or benzothiazole derivative of at least about 65%, 67%, 68%, 69%, 70%, 71%, 72%, 73%, 74%, 75%, 76%, 77%, 78%, 80%, 81%, 82%, 83%, 84%, 85%, 86%, 87%, 88%, 89%, or 90%.

In this regard, the present synthetic process can be employed for starting materials having two C=S group, two C=O, groups, one C=S and one C=O group, and the like, including the synthesis of dithiazoles due to S—S bond formation, for example according to the scheme:

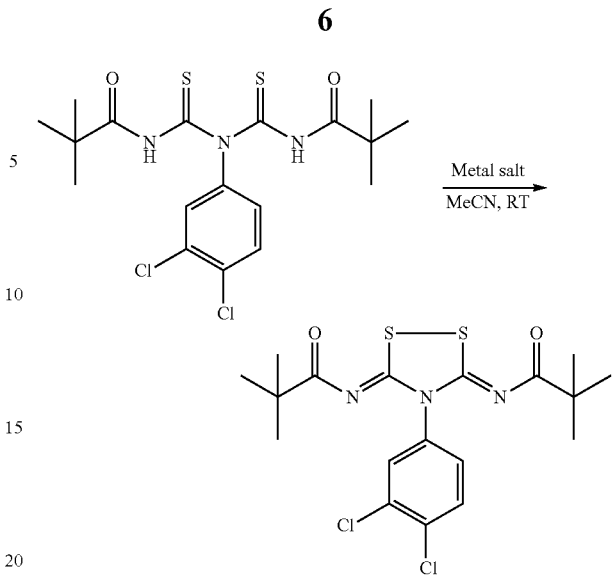

In further embodiments, the present synthetic scheme can be used to obtain a variety of derivatives 6-membered rings having one or more N, O, and/or S atoms therein. These methods can also be used to obtain NNS- or NS-containing 5-membered rings, with an additional function of Ar—C=O function (Ar=aromatic). Despite of the presence of C=O and C=S groups in the same molecule, the C=S group can selectively be converted into benzothiazole, thiadiazoles, and other heterocycles.

In another embodiment, once the thiazole, thiadiazole, or benzothiazole derivative is recrystallized, the structure of the compound can be confirmed through NMR spectroscopy and/or X-ray single crystal analysis. In certain embodiments, the recrystallization process is a slow evaporation recrystallization process, wherein the chloroform solvent is slowly evaporated over one, two, three, or more days to obtain the crystalline product.

In one embodiment, the present subject matter relates to a process for synthesizing N-(2H-thiazolo[3,2-b][1,2,4]thiadiazol-2-ylidene)benzamide comprising reacting 1-Benzoyl-3-(thiazole-2-yl)thiourea with auric chloride according to the following reaction and according to the general reaction steps defined above:

In an embodiment in this regard, the reaction mixture of the 1-Benzoyl-3-(thiazole-2-yl)thiourea and auric chloride can be stirred for at least six hours, at least seven hours, at least eight hours, or longer. Further, this synthetic scheme can provide an about 85% yield of the N-(2H-thiazolo[3,2-b][1,2,4]thiadiazol-2-ylidene)benzamide.

In another embodiment, the present subject matter relates to a process for synthesizing N-(6-methylthiazolo[4,5-b][1, 2,4]pyridin-2-yl)benzamide comprising reacting 1-(6-Methylpyridine-2-yl)-3-benzoylthiourea with auric chloride according to the following reaction and according to the general reaction steps defined above:

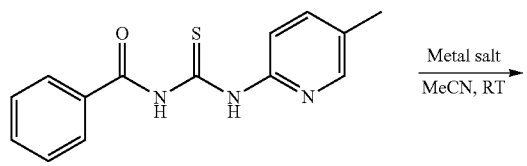

In an embodiment in this regard, the reaction mixture of the 1-(6-Methylpyridine-2-yl)-3-benzoylthiourea and auric chloride can be stirred for at least six hours, at least seven hours, at least eight hours, or longer. In another embodiment, the 1-(6-Methylpyridine-2-yl)-3-benzoylthiourea and the auric chloride can be reacted in an about 1:1 molar ratio. Further, this synthetic scheme can provide an about 68% yield of the N-(6-methylthiazolo[4,5-b][1,2,4]pyridin-2-yl)benzamide.

In still another embodiment, the present subject matter relates to a process for synthesizing N-(6-methoxy-3-(4-methoxyphenyl)-3λ4-benzo[d]thiazol-2-yl)benzamide gold (III) chloride comprising reacting 1-(Bis(4-methoxyphenyl)-3-benzoylthiourea with auric chloride according to the following reaction and according to the general reaction steps defined above:

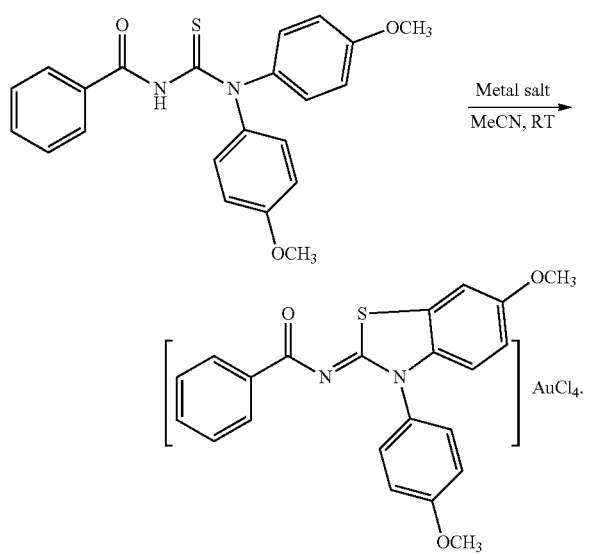

In an embodiment in this regard, the reaction mixture of the 1-(Bis(4-methoxyphenyl)-3-benzoylthiourea and auric chloride can be stirred for at least six hours, at least seven hours, at least eight hours, or longer. In another embodiment, the 1-(Bis(4-methoxyphenyl)-3-benzoylthiourea and the auric chloride can be reacted in an about 1:1 molar ratio. Further, this synthetic scheme can provide an about 70% yield of the N-(6-methoxy-3-(4-methoxyphenyl)-3λ4-benzo[d]thiazol-2-yl)benzamide gold(III) chloride.

In yet another embodiment, the present subject matter relates to a process for synthesizing 5-Methyl-N-phenyl-4λ4-[1,2,4]thiadiazolo[2,3-a]pyridine-2-aminegold(III) chloride comprising reacting 1-phenyl-3-(thiazole-2-yl)thiourea with auric chloride according to the following reaction and according to the general reaction steps defined above:

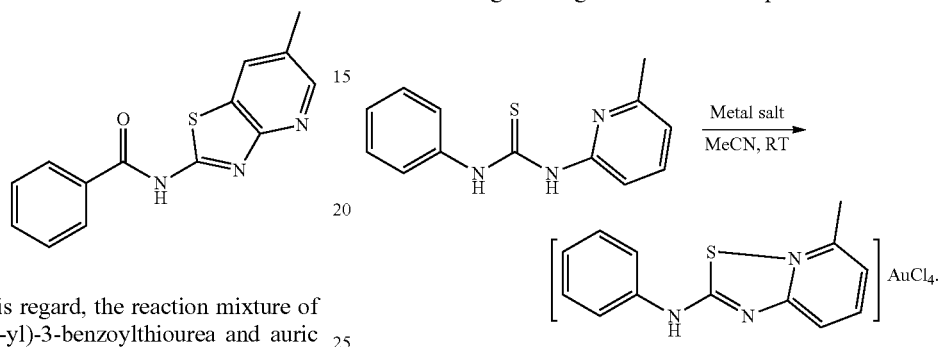

In an embodiment in this regard, the reaction mixture of the 1-phenyl-3-(thiazole-2-yl)thiourea and auric chloride can be stirred for at least six hours, at least seven hours, at least eight hours, or longer. In another embodiment, the 1-phenyl-3-(thiazole-2-yl)thiourea and the auric chloride can be reacted in an about 1:1 molar ratio. Further, this synthetic scheme can provide an about 69% yield of the 5-Methyl-N-phenyl-4λ4-[1,2,4]thiadiazolo[2,3-a]pyridine-2-aminegold(III) chloride.

EXAMPLES

Example 1

Synthesis of N-(2H-Thiazole[3,2-b][1,2,4]thiadiazol-2-ylidene)benzamide

A 1-benzoyl-3-(thiazole-2-yl)thiourea (131.50 mg, 0.5 mmol) solution in dry acetonitrile (CH$_3$CN) was slowly added to auric chloride (170.0 mg, 0.25 mmol) solution in acetonitrile. The reaction mixture was allowed to stir constantly, after a few minutes orange precipitates appeared in the reaction mixture, which was further allowed to stir for 8 hours to get maximum product. The product was then filtered and dried in open air. The solid product was then dissolved in chloroform and golden needle-like crystals with suitable dimensions were obtained after recrystallization. Structure of the compound was confirmed through NMR spectroscopy and X-ray single crystal analysis. The desired compound was formed as a result of cyclization of thiourea molecules in the presence of Au salt. Formula: $C_{11}H_7N_3OS_2$; Molar Mass: 261.32; Color: Orange; Yield=85%; Melting point=290-292° C.; 1HNMR: (Acetone-d6): δ (ppm)=6.75-6.73 (d, 1H, thiazole), 7.45-7.42 (t, 2H, CH, Ph), 7.62-7.59 (m, 1H, CH Ph) 7.67-7.65 (m, 2H, Ph), 7.70-7.65 (d, 1H, thiazole); $^{13}$CNMR (Acetone): δ (ppm)=182.4, 173.1, 164.3, 136.5, 131.6, 129.6, 128.6, 125.1, 115.5.

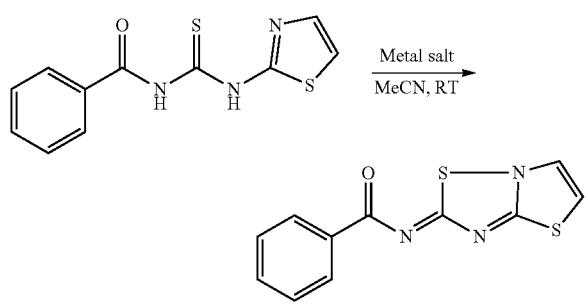

Example 2

Synthesis of N-(6-Methylthiazolo[4,5-b]pyridine-2-(3H)-ylidene)benzamide 1-(6-Methylpyridine-2-yl)-3-benzoylthiourea (270 mg, 1 mmol) was treated with HAuCl$_4$ (340.0 mg, 1 mmol) according to the same procedure as for Example 1. The crystalline product was studied with the help of $^1$HNMR and FTIR. Formula: C$_{14}$H$_{11}$N$_3$OS; Molar Mass: 269.32; Color; orange; Yield: 68%; Melting point=230° C.; FT-IR (cm$^{-1}$)= 3240, 3130, 1685, 1619, 1579, 1533, 1454, 1313, 1242, 710, 1052; $^1$HNMR: (Acetone-d$_6$): δ (ppm)=2.92 (s, 3H, CH3), 7.29-726 (d, 1H, NH), 7.66-7.54 (m, 2H, CH), 7.71-7.68 (d, 1H, Ph), 8.07-7.95 (m, 3H, Ph), 8.39-8.35 (m, 1H, Ph); $^{13}$CNMR (Acetone-d$_6$): δ (ppm)=178.0, 177.3, 146.0, 139.0, 134.0, 129.0, 128.0, 116.5, 116.4, 116.2, 20.0.

Example 3

Synthesis of N-(6-methoxy-3-(4-methoxyphenyl)-3λ4-benzo[d]thiazol-2-yl)benzamide gold(III) chloride 1-(Bis(4-methoxyphenyl)-3-benzoylthiourea (391.0 mg, 1.00 mmol) was added to an auric chloride, HAuCl$_4$, solution in acetonitrile (340.0 mg, 1 mmol) in a 1:1 molar ratio. The reaction mixture was stirred constantly. After a few seconds orange color precipitates appeared. The stirring was continued for the next 6 hours to complete the reaction. After completion of the reaction the precipitates were separated through filtration. The product was dried and then recrystallized in chloroform. The solvent was evaporated slowly and after a few days, orange needle-like crystals were grown. The crystals were analyzed through single analysis and NMR for structural confirmation. Formula: C$_{22}$H$_{18}$AuCl$_2$N$_2$O$_3$S; Molar Mass: 729.20; Color; orange; Yield: 70%; Melting point=320-322° C.; FT-IR (cm$^{-1}$)= 3248, 2837, 1687, 1604, 1571, 1473, 1346, 1271, 1243, 1211, 1168, 1105, 1024, 958, 901, 817, 711, 689, 711, 689, 590, 550; $^1$HNMR: (Acetone-d$_6$): δ (ppm)=3.93 (s, 3H, OMe), 3.99 (s, 3H, OMe), 7.20-7.06 (m, 2H, Ph), 7.32 (d, 2H, Ph), 7.46 (t, J=7.5 Hz, 2H, Ph), 7.57-7.59 (d, 1H, Ph), 7.69 (s, 3H, Ph), 8.00-8.03 (d, 2H, Ph).

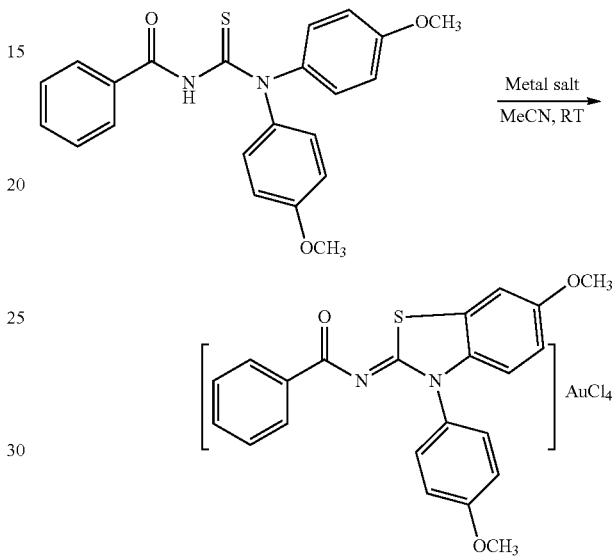

Example 4

Synthesis of 5-Methyl-N-phenyl-4λ4-[1,2,4]thiadiazolo[2,3-a]pyridine-2-aminegold(III) chloride 5-Methyl-N-phenyl-4λ4-[1,2,4]thiadiazolo[2,3-a]pyridine-2-aminegold(III) chloride was synthesized by treating 1-phenyl-3-(thiazole-2-yl)thiourea (243 mg, 1 mmol) with auric chloride (HAuCl4) (340.0 mg, 1 mmol) using the same procedure as followed for the above compounds. The compound was isolated as orange crystals and was analyzed through $^1$HNMR and single crystal analysis. Formula: C$_{13}$H$_{12}$N$_3$S; Molar Mass: 242.32; Color; orange; Yield: 69%; Melting point=230-232° C.; FTIR (cm$^{-1}$)=3193, 3069, 2851, 1631, 1612, 1558, 1534, 1454, 1379, 1335, 1249, 1152, 1057, 1034, 902, 834, 796, 756, 687, 584, 498; $^1$HNMR: (Acetone-d$_6$): δ (ppm)=2.91 (s, 3H, CH3), 7.34-7.29 (t, 1H, CH), 7.48-7.28 (m, 2H), 7.59-7.47 (m, 1H), 7.90-7.85 (m, 2H CH) 8.29-8.24 (m, 1H), 8.05-8.00 (d, 1H), 12.21 (br, 1H, NH).

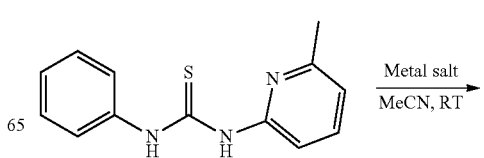

-continued

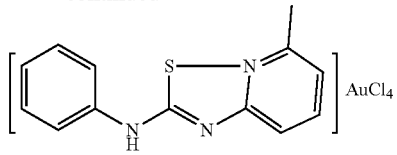

It is to be understood that the present subject matter, comprising various synthetic methods, is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A process for synthesizing a thiadiazole, the process comprising:
   preparing a first solution of a thiourea compound in acetonitrile;
   preparing a second solution of auric chloride (HAuCl$_4$) in acetonitrile;
   adding the first solution to the second solution to obtain a reaction mixture;
   stirring the reaction mixture for at least six hours;
   filtering the reaction mixture to obtain a solid product;
   dissolving the solid product in chloroform to obtain a third solution; and
   recrystallizing the thiadiazole from the third solution;
   wherein the thiourea compound is 1-Benzoyl-3-(thiazole-2-yl)thiourea, the thiadiazole is N-(2H-thiazolo[3,2-b][1,2,4]thiadiazol-2-ylidene)benzamide, and the process comprises the following reaction:

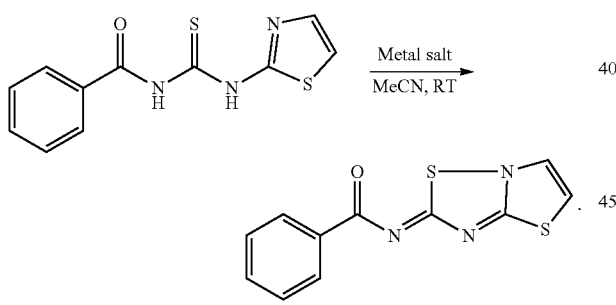

2. The process of claim 1, wherein the thiadiazole is formed as a result of cyclization of the thiourea compound in the presence of an Au salt from the auric chloride.

3. The process of claim 1, wherein a cyclic group of the dithiazole is prepared by forming any of a S—N, S—C, S—S, or S—O bond.

4. The process of claim 1, wherein C=S groups in the thiourea compound are selectively converted into forming the thiadiazole.

5. The process of claim 1, wherein the reaction is carried out at room temperature.

6. The process of claim 1, wherein the reaction mixture is stirred for at least eight hours.

7. The process of claim 1, providing an about 85% yield of the N-(2H-thiazolo[3,2-b][1,2,4]thiadiazol-2-ylidene)benzamide.

8. A process for synthesizing a thiadiazole, the process comprising:
   preparing a first solution of a thiourea compound in acetonitrile;
   preparing a second solution of auric chloride (HAuCl$_4$) in acetonitrile;
   adding the first solution to the second solution to obtain a reaction mixture;
   stirring the reaction mixture for at least six hours;
   filtering the reaction mixture to obtain a solid product;
   dissolving the solid product in chloroform to obtain a third solution; and
   recrystallizing the thiadiazole from the third solution;
   wherein the thiourea compound is 1-phenyl-3-(thiazole-2-yl)thiourea, the thiadiazole is 5-Methyl-N-phenyl-4$\lambda^4$-[1,2,4]thiadiazolo[2,3-a]pyridine-2-aminegold(III) chloride, and the process comprises the following reaction:

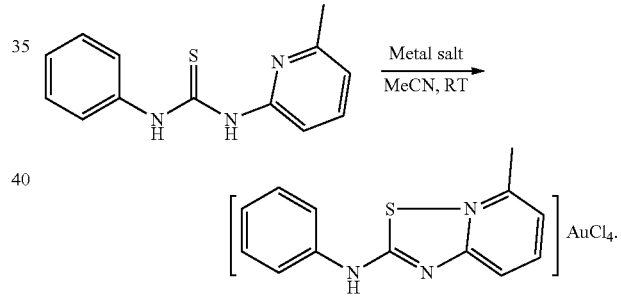

9. The process of claim 8, wherein the 1-phenyl-3-(thiazole-2-yl)thiourea and the auric chloride are reacted in an about 1:1 molar ratio.

10. The process of claim 8, providing an about 69% yield of the 5-Methyl-N-phenyl-4$\lambda^4$-[1,2,4]thiadiazolo[2,3-a]pyridine-2-aminegold(III) chloride.

* * * * *

UNITED STATES PATENT AND TRADEMARK OFFICE
CERTIFICATE OF CORRECTION

PATENT NO. : 11,958,866 B1
APPLICATION NO. : 18/381016
DATED : April 16, 2024
INVENTOR(S) : Awal Noor, Ezzat Khan and Umar Ali Khan Page 1 of 1

It is certified that error appears in the above-identified patent and that said Letters Patent is hereby corrected as shown below:

On the Title Page

Item (72) Inventors, please delete the second Inventor city "Al-Ahsa, (SA)" and replace with "Sakhir, (BH)".

Item (72) Inventors, please delete the third Inventor city "Al-Ahsa, (SA)" and replace with "Malakand, (PK)".

Signed and Sealed this
Sixteenth Day of July, 2024

Katherine Kelly Vidal
*Director of the United States Patent and Trademark Office*